(12) United States Patent
Melsheimer

(10) Patent No.: US 9,445,801 B2
(45) Date of Patent: Sep. 20, 2016

(54) MEDICAL DEVICE WITH SELECTIVE RIGIDITY

(71) Applicant: Cook Medical Technologies LLC, Bloomington, IN (US)

(72) Inventor: Jeffrey S. Melsheimer, Springville, IN (US)

(73) Assignee: COOK MEDICAL TECHNOLOGIES LLC, Bllomington, IN (US)

( * ) Notice: Subject to any disclaimer, the term of this patent is extended or adjusted under 35 U.S.C. 154(b) by 103 days.

(21) Appl. No.: 14/203,007

(22) Filed: Mar. 10, 2014

(65) Prior Publication Data

US 2014/0277384 A1     Sep. 18, 2014

Related U.S. Application Data

(60) Provisional application No. 61/791,561, filed on Mar. 15, 2013.

(51) Int. Cl.
| | |
|---|---|
| *A61B 1/32* | (2006.01) |
| *A61B 17/02* | (2006.01) |
| *A61F 2/82* | (2013.01) |
| *A61F 2/90* | (2013.01) |

(52) U.S. Cl.
CPC ............. *A61B 17/0218* (2013.01); *A61F 2/82* (2013.01); *A61B 2017/0225* (2013.01); *A61F 2/90* (2013.01); *A61F 2250/0003* (2013.01); *A61F 2250/0018* (2013.01)

(58) Field of Classification Search
CPC .......... A61B 17/0218; A61B 17/3423; A61B 17/3431; A61B 2017/00557; A61B 2017/00561; A61B 2017/00566
USPC ................................................. 600/201–246
See application file for complete search history.

(56) References Cited

U.S. PATENT DOCUMENTS

| | | | |
|---|---|---|---|
| 4,984,564 A * | 1/1991 | Yuen | A61B 17/0293 600/207 |
| 5,275,610 A | 1/1994 | Eberbach | |
| 5,312,432 A | 5/1994 | Pingleton et al. | |
| 5,582,577 A | 12/1996 | Lund et al. | |
| 6,293,968 B1 | 9/2001 | Taheri | |
| 8,425,412 B2 | 4/2013 | Rucker | |

(Continued)

FOREIGN PATENT DOCUMENTS

WO   WO 2012/071105 A1   5/2012

OTHER PUBLICATIONS

International Search Report for PCT/US2014/023159, dated Mar. 9, 2014, 3 pp.

(Continued)

*Primary Examiner* — Ellen C Hammond
*Assistant Examiner* — Christina Negrellirodrigue
(74) *Attorney, Agent, or Firm* — Brinks Gilson & Lione

(57) ABSTRACT

A device for obtaining selective rigidity with respect to a patient is provided. The device includes a scaffold that is arranged to be flexible when in a first relaxed configuration, wherein the scaffold is configured to become substantially more rigid when a suction force is applied thereto. The scaffold comprises first and second opposing outer flexible layers that are sealed together to form a plurality of elongate pockets therein, and an expanded structure disposed within the plurality of elongate pockets and in communication with a vacuum port that receives the suction force.

20 Claims, 7 Drawing Sheets

(56) References Cited

U.S. PATENT DOCUMENTS

| | | |
|---|---|---|
| 8,758,235 B2 | 6/2014 | Jaworek |
| 8,968,188 B2 * | 3/2015 | Rockrohr ........... A61B 17/3423 600/205 |
| 2009/0149710 A1 | 6/2009 | Stefanchik |
| 2012/0238825 A1 * | 9/2012 | Smith ................ A61B 17/3423 600/207 |

OTHER PUBLICATIONS

Brown, Eric et al., Universal robotic gripper based on the jamming of granular material, PNAS, Nov. 2, 2010, vol. 107, No. 44, pp. 18809-18814.

International Preliminary Report on Patentability including the Written Opinion for PCT/US2014/023159, dated Sep. 15, 2015, 7pgs.

* cited by examiner

MEDICAL DEVICE WITH SELECTIVE RIGIDITY

CROSS-REFERENCE TO RELATED APPLICATIONS

This application claims priority from U.S. provisional application No. 61/791,561, filed on Mar. 15, 2013, the entirety of which is hereby fully incorporated by reference herein.

TECHNICAL FIELD

This disclosure relates to expandable and compressible structures for clinical use with respect to a patient.

BRIEF SUMMARY

A first representative embodiment of the disclosure is provided. The embodiment includes a device for obtaining selective rigidity with respect to a patient is provided. The device includes a scaffold that is arranged to be flexible when in a first relaxed configuration, wherein the scaffold is configured to become substantially more rigid when a suction force is applied thereto. The scaffold comprises first and second opposing outer flexible layers that are sealed together to form a plurality of elongate pockets therein, and an expanded structure disposed within the plurality of elongate pockets and in communication with a vacuum port that receives the suction force.

Advantages of the present disclosure will become more apparent to those skilled in the art from the following description of the preferred embodiments of the disclosure that have been shown and described by way of illustration. As will be realized, the disclosed subject matter is capable of other and different embodiments, and its details are capable of modification in various respects. Accordingly, the drawings and description are to be regarded as illustrative in nature and not as restrictive.

DETAILED DESCRIPTION OF THE DRAWINGS AND THE PRESENTLY PREFERRED EMBODIMENTS

Turning now to FIGS. 1-7, a device 1 for obtaining selective rigidity with respect to a patient is provided. The device 1 may be used to assist with a medical procedure within an internal cavity of a patient (either a human, a mammal or other type of animal). Alternatively, the device 1 may be configured to be used to externally and in some embodiments temporarily with respect to a portion of a patient's anatomy.

Figure 1:
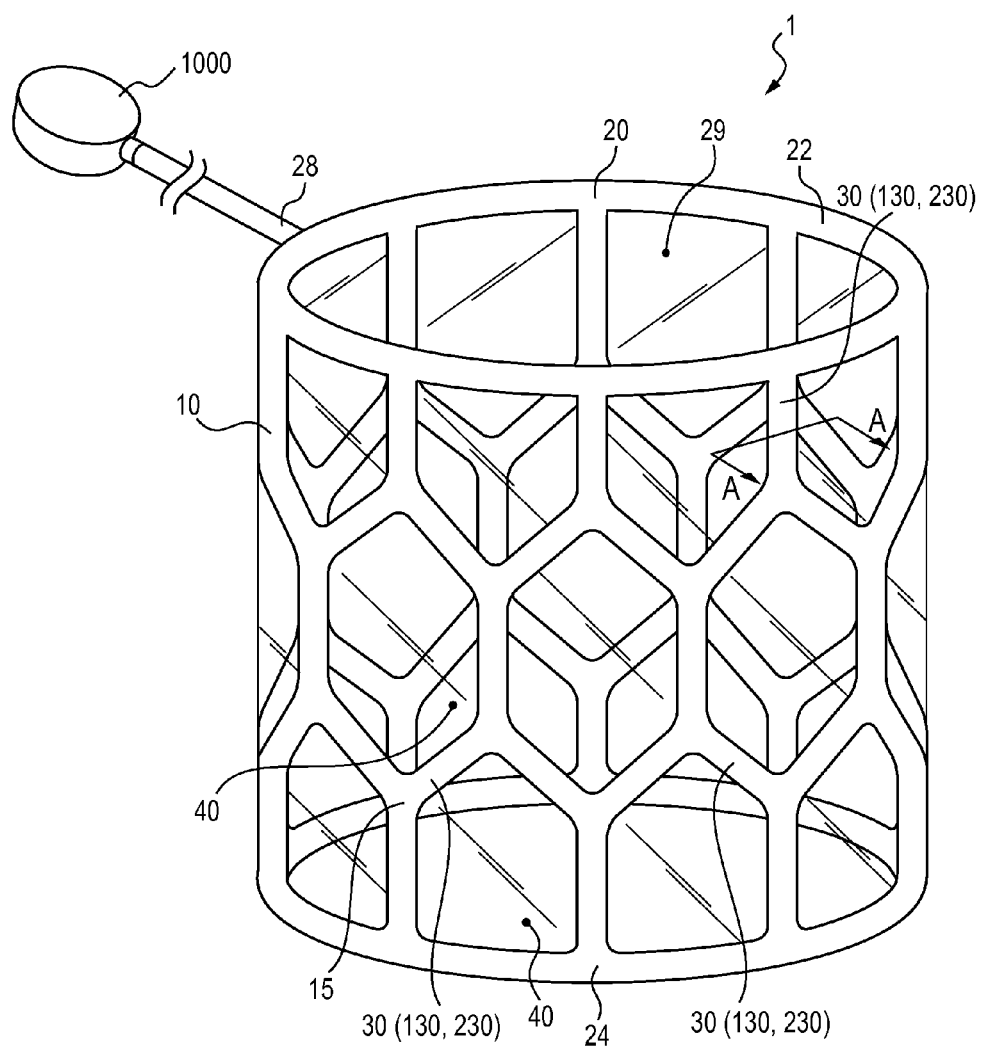
FIG. 1 is a perspective view of a device for selective rigidity formed as a cylinder.

In some embodiments, the device 1 may be formed into a tube or cylinder 10, as shown in FIG. 1. The cylinder 10 will be appreciated to be useful for various open surgical procedures, or various laparoscopic procedures. In some embodiments, the cylinder 10 may include opposed ends 22, 24, while in other embodiments, an extended end 24 (normally that extends further distally into the patient) may be closed, either with a window 40 (discussed below), or with a mesh or other suitable structure, while the opposite end 22 (e.g. an end closer to the vacuum line 28) is open. In other embodiments, both ends 22, 24 of the cylinder may be closed, such as in embodiments where the cylinder 10 is used to position tissue into a certain orientation or position, but where access within the cylinder 10 is not necessary.

By way of general example, in some clinical embodiments, the cylinder 10 may be configured to be used as an internal surgical retractor, or a flexible barrier that may be deployed within a surgical zone to isolate the surgical zone and neighboring tissue or viscera outside of the surgical zone. In other embodiments, the cylinder 10 may be configured to provide temporary or long term mechanical or radial support upon a structure or lumen, and act as a stent. In still other embodiments, the cylinder 10 may be configured to provide external mechanical support to a structure, or temporarily immobilize a structure, such as a cast or a splint.

Figure 2:
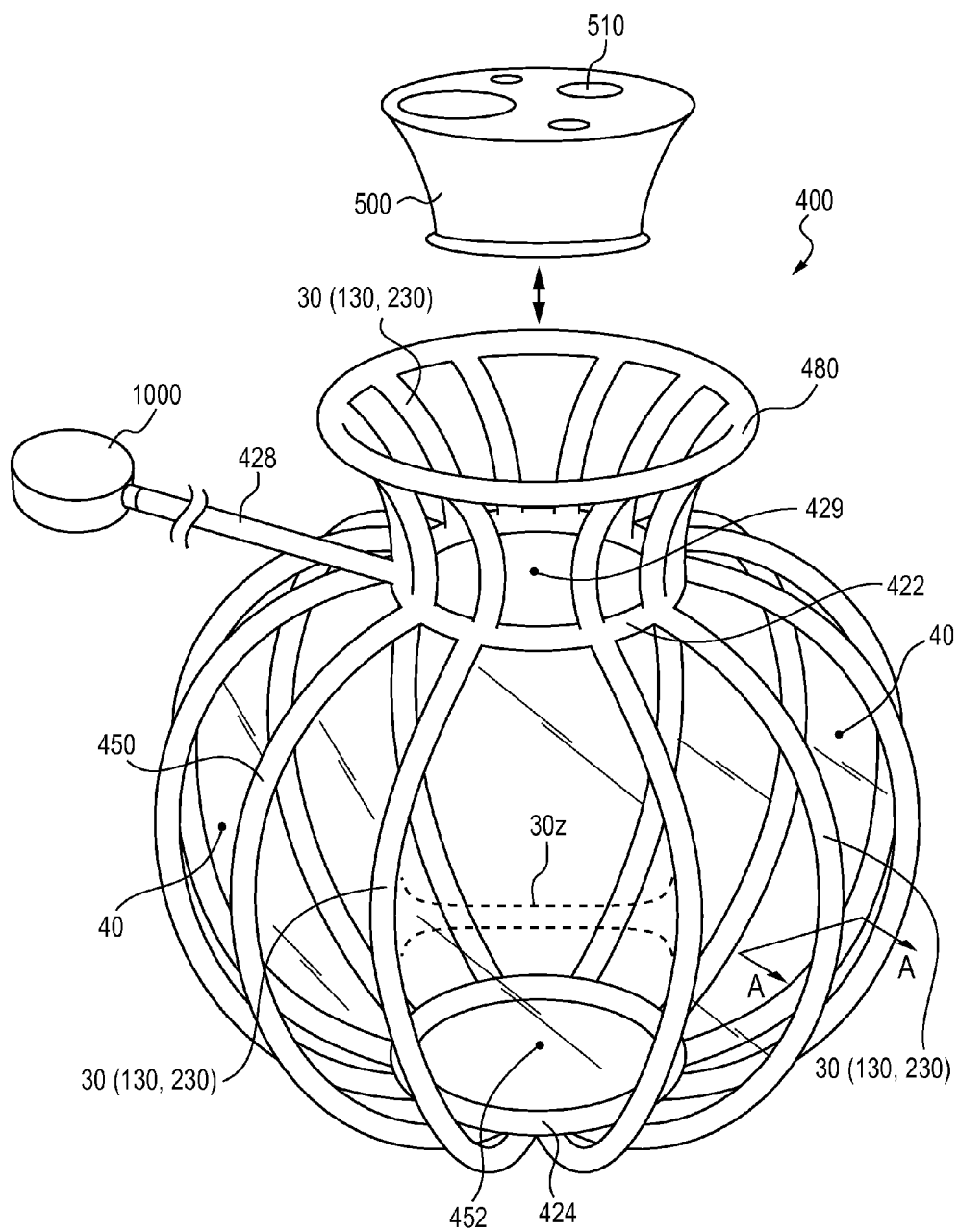
FIG. 2 is a perspective view of a device for selective rigidity formed as a sphere.

In other embodiments as shown in FIG. 2, the device 1 may be formed into a sphere 400 or a similar construction. Embodiments where the device is shaped as a sphere 400 will be appreciated to be applicable or useful for the same or related clinical uses as listed above with respect to the cylinder 10, or other clinical uses where a cylinder is not clinically indicated. By way of clinical example, the sphere 400 may be used as a retractor used during laparoscopic or open surgery. Alternatively, by way of example, the device may be formed as a semi-circle (i.e. half of a hollow sphere) where the device forms a somewhat rigid support structure, such as a bicycle helmet.

Figure 6:
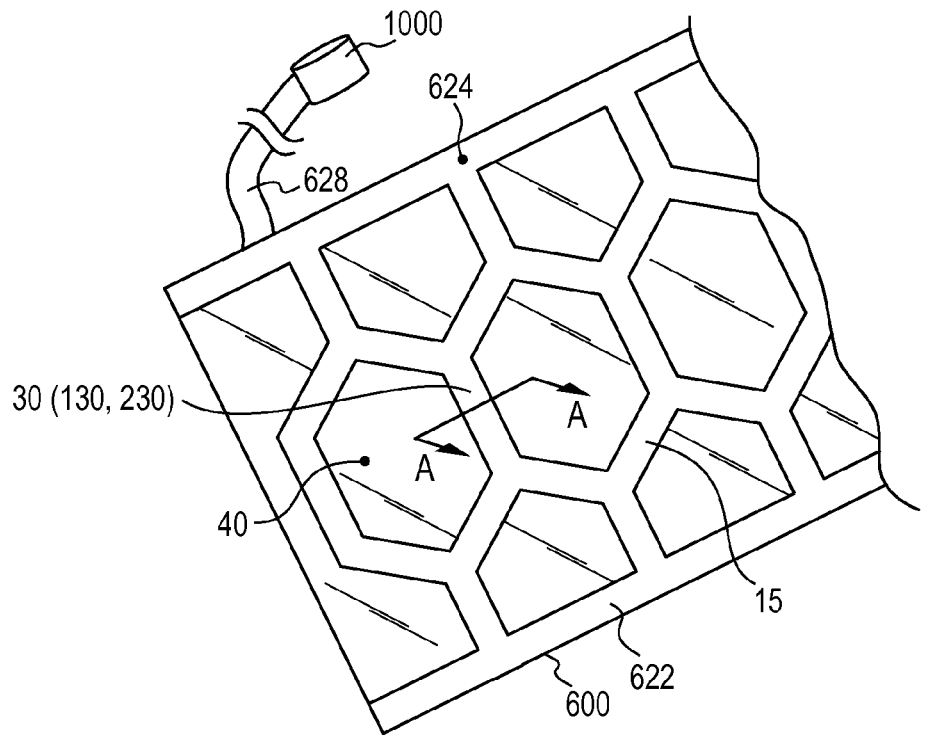
FIG. 6 is a perspective view of a device for selective rigidity formed as a flat sheet.
Figure 6A:
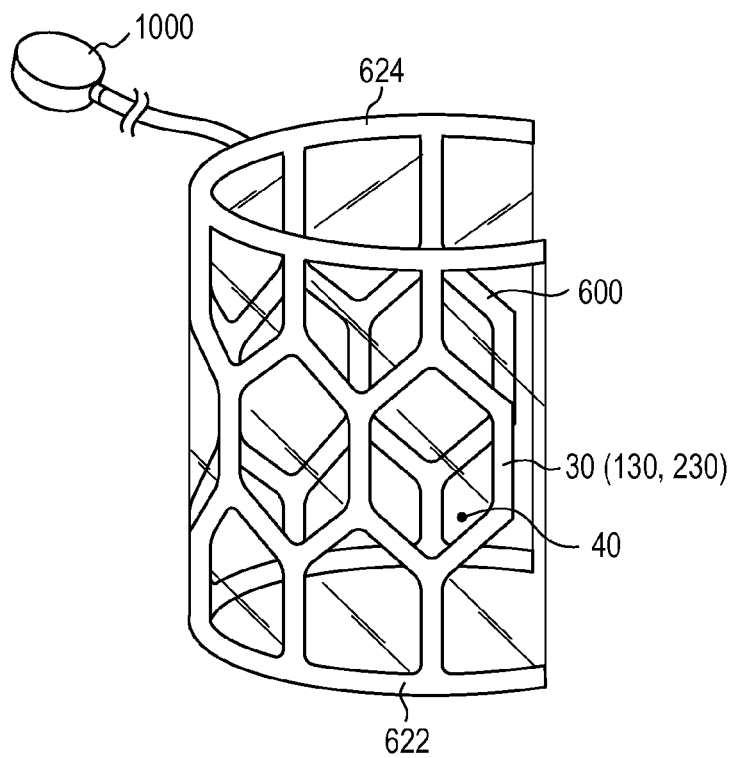
FIG. 6a is the device of FIG. 6 formed into a c-shape.

In still other embodiments shown in FIGS. 6a and 6b, the device 1 may be formed into a sheet 600, which can clinically implemented as a sheet, or can be clinically implemented with the sheet configured into a three-dimensional shape, such as a C-shape depicted on FIG. 6b.

The device 1 is configured to be maintained in a flexible orientation when a plurality of elongate pockets 30 (130, 230) that define a scaffold 15 of the device 1 are in the normal expanded configuration, but the device 1 is configured to become substantially more rigid, and configured to significantly maintain a set geometry when the elongate pockets 30 (130, 230) are placed in communication with a source of suction, which withdraws a significant portion of the air (or other gasses) present within the internal volume 50 of the elongate pockets 30 (130, 230). The device 1 is configured to retain its normal flexibility when the suction is released from the elongate pockets 30 (130, 230), which allows the evacuated air to return to within the internal volume of the elongate pockets 30.

In embodiments where the device is used as a retractor during laparoscopic surgery, the device 1 should be sufficiently compressible into a small cylindrical cross-section to fit through a typical laparoscopic port. This compressibility of the device 1 is based upon the overall compressibility of the foam (or another compressible material) used within the pockets 30 (130, 230), discussed below, and the device 1 can expand on its own when within the patient. In some embodiments, the device 1 may be made to be expandable (particularly after being compressed to extend through a port) by "inflating" the plurality of pockets 30 (discussed below) using the vacuum port 28. In embodiments where the device 1 used in laparoscopic surgery or even in open surgery the vacuum port 28 is configured to communicate outside of the patient to connect to a convenient source of suction 1000 (or positive pressure as discussed above).

Each of the cylinder 10, the sphere 400, or the sheet 600 may be made from the same or a related scaffold 15 design to form the same or similar elongate pockets 30 (130, 230), which are depicted upon the respective cylinder 10, sphere 400, or sheet 600 through section A-A (FIGS. 1, 2, and 6*a*, respectively). In some embodiments, the scaffold 15 may be formed like a honeycomb, with a plurality of elongate pockets 30 connected together that form structural walls and the spacing between neighboring elongate pockets 30 define a plurality of windows 40. As shown in FIG. 1, the scaffold 15 may be formed with multiple windows 40 arranged across the height of the scaffold 15, between a first end 22 and a second end 24, with the windows 40 staggered, or offset, between the upper and lower ends 22, 24 of the scaffold 15. As discussed herein, in some embodiments, each of the plurality of pockets 30 are fluidly connected together along the scaffold 15, while in other embodiments the pockets 30 are fluidly connected in a groupwise manner.

In other embodiments, the windows 40 may be configured to be aligned along the height and circumference of the scaffold 15, such as a scaffold 15 that defines a plurality of windows 40 that are shaped as stacked squares or rectangles. As will be understood by those skilled in the art with a thorough review of this application, scaffold 15 designs with staggered windows 40 (i.e. like a honeycomb) might be stronger in certain directions (or potentially in all directions) in parallel to the sheets 42, 44 forming the scaffold 15, and potentially in the directions radially into and/or out of the cylinder 10 and therefore better suited for some applications/shapes of the device 1, while designs with stacked windows 40 may be of different/less strength than the staggered design and therefore better suited for use with other applications/shapes of the device 1.

In other embodiments, for example, in some embodiments where the scaffold 15 forms a sphere (e.g. FIG. 2) the scaffold 15 may be formed from a plurality of elongate pockets 30 (130, 230) that form ribs that linearly extend from top 422 to the base 424 of the sphere (to define the curved surface of the sphere), which may form windows 40 that also extend from the top 422 to the base 424 of the sphere. In other embodiments, the scaffold 15 may further include a plurality of horizontal ribs (30*z*, one potential horizontal rib shown in broken lines on FIG. 2) to provide additional structural support to the scaffold 15 and to decrease the size of the windows 40.

In some embodiments, the device 1, such as the cylinder 10 or the sphere 400, as shown in FIG. 2, may receive a cap 500 that removably closes a portion or all of the open top 422 of the device 1. By way of example, the cap 500 may be used in situations where the device 1 is used as a retractor for open surgery, but it is desired to insufflate the abdomen during open surgery or to limit the overall exposure of the surgical field to the atmosphere. In this instance, the cap 500 may include one or more ports 510 that act as laparoscopic ports. In situations where the device 1 is configured to receive a cap 500, the device 1 (such as the spherical embodiment 400 shown in FIG. 2), may include a support 480 (either made from the plurality of pockets 30, or from other structure attached to the device) that supports the cap 500, and may extend outside of the patient during use.

The scaffold 15 may be constructed such that all of the elongate pockets 30 (130, 230) that define the structural walls of the scaffold 15 are fluidly connected, such that a suction (or vacuum force) that is applied to a portion of the scaffold 15 communicates throughout the entire scaffold 15. In other embodiments, the scaffold 15 may be formed from two or more independent fluid zones, wherein each elongate pocket 30 within a single zone is fluidly connected, but multiple zones within a single scaffold 15 are not directly fluidly connected. In embodiments with multiple fluid zones, each fluid zone may be connected to the same vacuum source (shown schematically as 1000) through a common vacuum port 28, or through separate vacuum ports 28 that connect to the vacuum source through a common header (or different vacuum sources 1000). As will be appreciated, embodiments with scaffolds 15 that define multiple fluid zones may be useful for the sake of redundancy, such that a loss of suction (either due to a leak or blockage along a portion of an elongate pocket 30) in one fluid zone (which, as discussed below may cause the scaffold 15 in that zone to lose all or a portion of its rigidity) will not lose suction (rigidity) in the remaining zones.

In some embodiments, the scaffold 15 may be constructed from two thin parallel sheets 42, 44 of flexible material that are aligned in over or next to each other. The two sheets of material 42, 44 (such as polyethylene (Mylar), Nylon, or PVA, or other suitable materials are bonded or heat sealed together along various edges 48*a* to define windows 40, and to define elongate pockets 30 (130, 230), which are defined between two parallel seams 48*a*. The thin sheets 42, 44 may each be about 0.005 to about 0.002 inches thick (inclusive of all thicknesses within this range), or may be a thicker material that is still sufficiently flexible to allow a vacuum to be drawn within the elongate pockets 30, and to accept the desired shape of the device 1. In some embodiments, the first and second sheets 42, 44 may be sealed together throughout the entire area of each window 40, while in other embodiments, the first and second sheets 42, 44 are only sealed together to define each seam 48*a*. Finally, in some embodiments sheets 42, 44 forming the windows 40 within the scaffold 15 may be cut (without cutting the seams 48*a*) to allow for access through the device, such as through a retractor, to access a portion of the viscera outside of the retractor.

In some embodiments, the seams 48*a* are constructed to be substantially air-tight. In some embodiments, an elongate wire or cord 48 may be disposed between the two sheets of material 42, 44 where the seam 48*a* is to be formed. When provided, the wire or cord 48 provides a surface upon which both opposite sheets of material 42, 44 are sealed to prevent any discontinuities in the sealed edge 48*a* (that could leak air therethrough) or to block air flow in situations where small discontinuities in the seal 48 exist. In other embodiments, the two sheets 42, 44 may be sealed directly together along the sealed edge 48*a*.

The pockets 30 (130, 230) may include a volume of foam or other expanded and compressible material that is disposed upon the length of the elongate pocket 30. The compressible material may be a foam, such as an open cell foam formed with a plurality of voids (schematically as 56 in FIG. 3a) distributed throughout the volume of the foam. Some suitable materials may be expanded polyethylene, or foams made of other expanded materials. In some embodiments polyester foams may be suitable, such as known "acoustic" foam. In other embodiments, the compressible material may be a plurality of small particles, granules, pellets, ground-material such as bio-compatible expanded foam pellets, coarse-ground coffee, poly vinyl alcohol (PVA) granules, or polymeric regular polyhedrons peanuts, or similar regular or irregular shaped rigid pieces, which will jam against one another when compressed by an overlying film and resist sliding past one another and are relatively light in weight for their given volume.

Figure 3A:
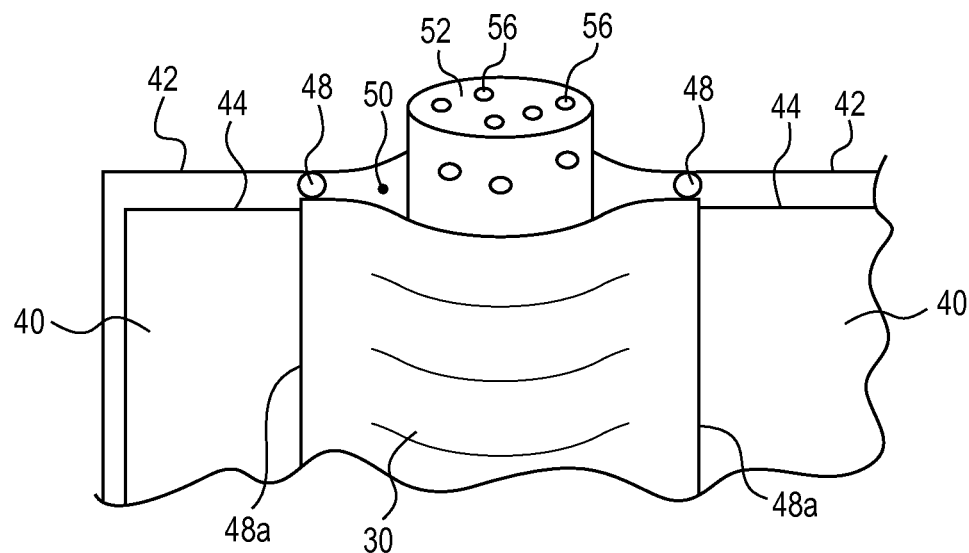
FIG. 3a is a view of a portion of an elongate pocket along section A-A of any one of FIG. 1, 2, or 6 in a normal configuration.
Figure 3B:
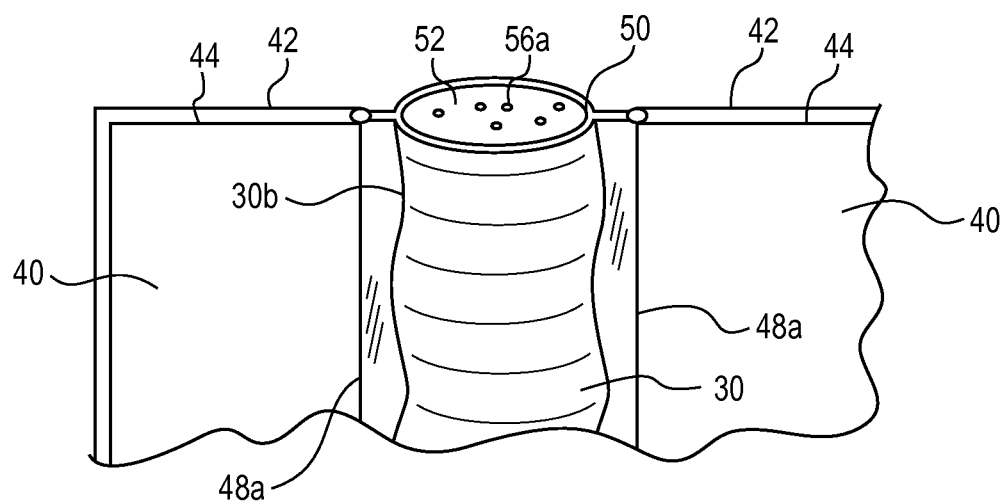
FIG. 3b is the view of FIG. 3a in the influence of a suction force.

A first configuration for an elongate pocket 30 is depicted in FIGS. 3a and 3b. The pocket 30 is defined by two elongate seams along parallel edges 48a, which are formed by bonding or sealing the two sheets of material 42, 44 therealong. The pocket 30 includes an internal volume, which receives one or more cylindrical strips of foam 52 or other type of expanded and collapsible structure (such as foam 52 or other materials) that extends along the length of the pocket 30. The foam 52 may be round in cross-section, or in other embodiments oval, elliptical, arcuate, square, or other thin polygonal shapes in cross-section. As shown schematically in FIG. 3a, the foam 52 includes a plurality of voids 56, normally filled with air when the foam 52 is in its normal expanded state, and due to the circular cross-section of the foam 52 with respect to the pocket 30, the pocket includes empty portions 50 between each seal 48a and each opposite radial side of the foam 52.

As shown in FIG. 3a, the pocket 30 (and therefore the scaffold 15 as a whole) is substantially flexible when in the normal configuration, due to the normal flexibility of the foam 52 and the air within the empty portions 50 of the pocket 30. As shown in FIG. 3b, when a suction is drawn within the pocket 30, the plurality of voids 56 in the foam 52 are compressed (as shown schematically as 56a) due to the air being withdrawn from within the foam 52, as well as the air withdrawn from the open spaces within the pocket 30. As a result of the air being withdrawn, the walls of the pocket 30 are pushed toward the compressed foam 52 (due to the relatively larger air pressure outside of the pocket 30 than within the pocket 30), and the compressed foam 52 becomes significantly more rigid (due to the collapse of the air gaps 56, which normally are compressed and expanded with the application of only minimal force to the foam 56), which causes the scaffold 15 to also become more rigid. As shown schematically as element 30b, the sheets 42, 44 defining the pocket 30 are pulled together, further increasing the rigidity and potentially changing the cross-section of the foam 52.

Figure 4A:
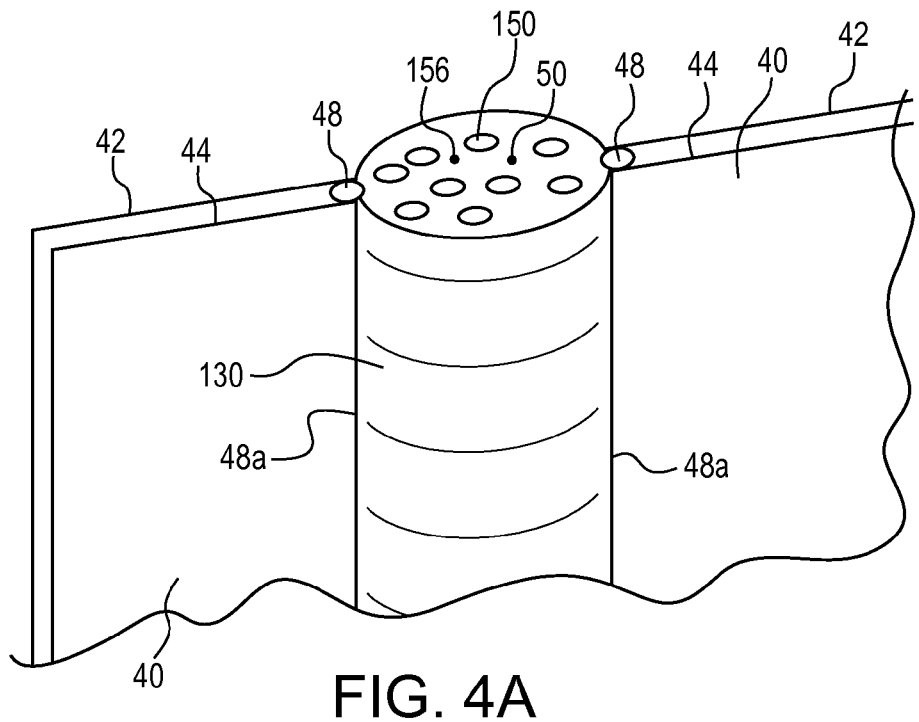
FIG. 4a is a view of another type of elongate pocket along section A-A of any one of FIG. 1, 2, or 6 in a normal configuration.
Figure 4B:
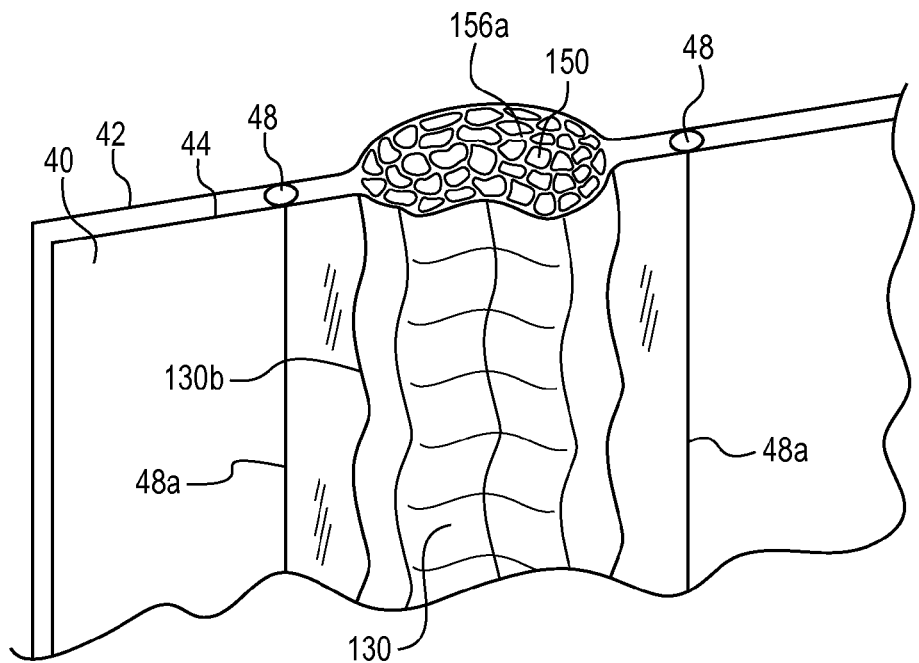
FIG. 4b is the view of FIG. 4a in the influence of a suction force.

Turning now to FIGS. 4a and 4b, another configuration for an elongate pocket 130 is depicted. The pocket 130 that is suitable for construction of a scaffold 15 is schematically depicted, in the normal flexible state (FIG. 4a) and in the rigid state (FIG. 4b) due to the application of a suction to the pocket 130. The pocket 130 may be defined between two parallel seams 48a that may be formed as described elsewhere herein. The pocket 130 is full with a plurality of loosely packed pellets 150 peanuts, balls, or other types of small discrete structures of foam or another compressible and flexible material. When resting within the pocket 130 a plurality of spaces are present between neighboring pellets 150, which allows the pocket 130 to be flexible due to the ease of realignment of the plurality of pellets 150 within the pocket 130.

As shown in FIG. 4b, when a suction is drawn within the pocket 130, the volume of the pocket 130 is compressed due to the higher relative pressure outside of the pocket 130 than within the pocket 130. Further, in embodiments where the pellets 150 are formed from foam, any voids (not shown, but similar to voids 56 within the foam 52, discussed above) within the foam pellets 150 are compressed due to the air being evacuated from within the pellets 150. The compression of the pellets 150 urges contraction, and to more tightly fit together, as further urged together by the reduction of air within the pocket 130. The combination of the increase in rigidity of individual pellets 150 and the overall tighter pack of neighboring pellets 150 (schematically in FIG. 4b as 156a) causes the rigidity within the pocket 130 to increase (which causes the rigidity of the scaffold 15 to increase). As depicted as element 130a, the sheets 42, 44 defining the pocket 130 may be pulled together as shown with element 130b, further increasing the rigidity of the pocket 130.

Figure 5A:
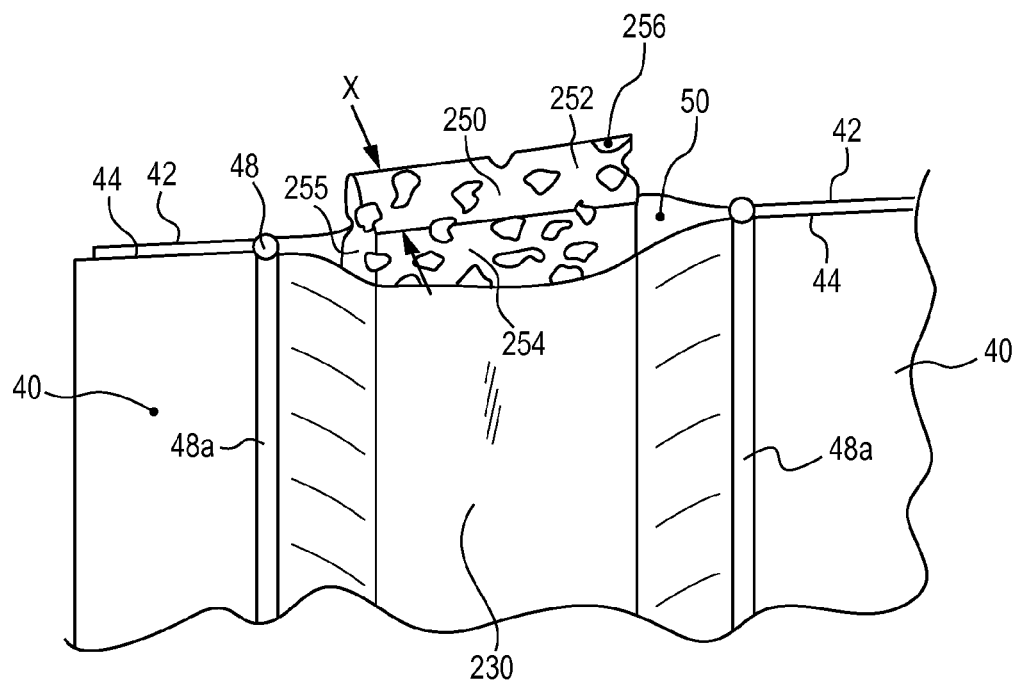
FIG. 5a is a view of another type of elongate pocket along section A-A of any one of FIG. 1, 2, or 6 in a normal configuration.
Figure 5B:
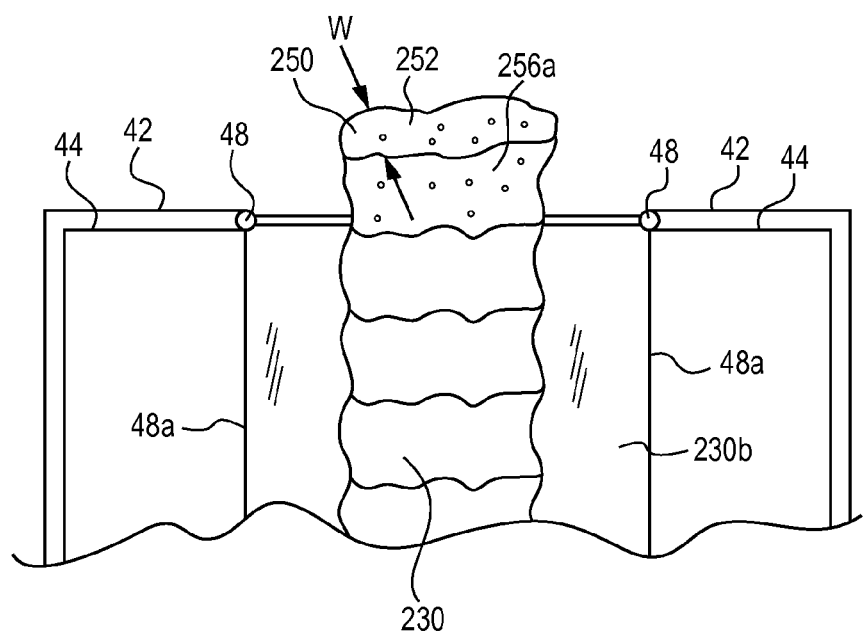
FIG. 5b is the view of FIG. 5a in the influence of a suction force.

Turning now to FIGS. 5a and 5b, another elongate pocket 230 is depicted. The pocket 230 that is suitable for construction of a scaffold 15 is schematically depicted, in the normal flexible state (FIG. 5a) and in the rigid state (FIG. 5b) due to the application of a suction to the pocket 230. As with the other pockets discussed above, the pocket 230 may be defined between two parallel seams 48a that may be formed as described elsewhere herein. The pocket 230 receives one or more elongate strips of foam 250 with a rectangular cross-section along its length. As with the foam 52 discussed above, the foam 250 may include a plurality of a voids 256 that are normally filled with air, that allow the expanded foam 250 to be easily expanded. In some embodiments, the foam 250 with the rectangular cross-section may be preferred to provide for increased strength in one direction and decreased strength in the perpendicular direction. For example, in the embodiment shown in FIG. 5a, the wider faces 254 are in parallel with the sheets 42, 44 that define the pocket 230 (and the windows), while the narrower faces 255 are perpendicular to the sheets 42, 44. As can be understood, the pockets 230 in this configuration will be more resistant to bending in a direction parallel with the sheets 42, 44 than a direction perpendicular to the sheets 42, 44 (i.e. into and out of the page displaying FIG. 5a) due to the larger thickness of the foam 250 in the direction parallel with the sheets 42, 44. Placement of the foam 250 in a perpendicular alignment would make the scaffold 15 more resistant to bending into or out of the page upon which FIG. 5a is printed.

As shown in FIG. 5b, when a suction is drawn within the pocket 230, the volume within the pocket 230 is compressed due to the higher relative pressure outside the pocket 230 than within the pocket 230. Further, the suction additionally causes the voids 256 within the foam 250 to collapse (as discussed above with respect to voids 56), which compresses the foam 250 and makes the foam 250 more rigid, which ultimately makes the pocket 230 and the scaffold 15 more rigid. Moreover, as shown schematically in FIG. 5b, the collapsing of the voids 256 may cause the foam 250 to establish a non-uniform cross-section, with somewhat arcuate faces, and may cause the width W of the compressed foam (FIG. 5b) to be less than the width X of the expanded foam (FIG. 5a). As shown with element 230b, the sheets 42, 44 forming the opposite walls of the pocket 230 are pulled together as the air is evacuated out of the pocket 230, further increasing the rigidity of pocket 230.

In some embodiments, the plurality of pockets 30 (130, 230) forming the scaffold 15 may be formed from different constructions within the same scaffold 15, such as portions formed with pockets 30 with portions also formed with pockets 130 and/or pockets 230. As will be appreciated, the use of different pockets with different flexibilities will render a scaffold 15 with specific relatively more or less strong or flexible portions as may be warranted for different design applications. In other embodiments, pockets may be formed with different structures within each pocket, such as, by way of example, the rectangular form 250 and a plurality of pellets 150 disposed outboard of the rectangular foam 250.

Figure 7:
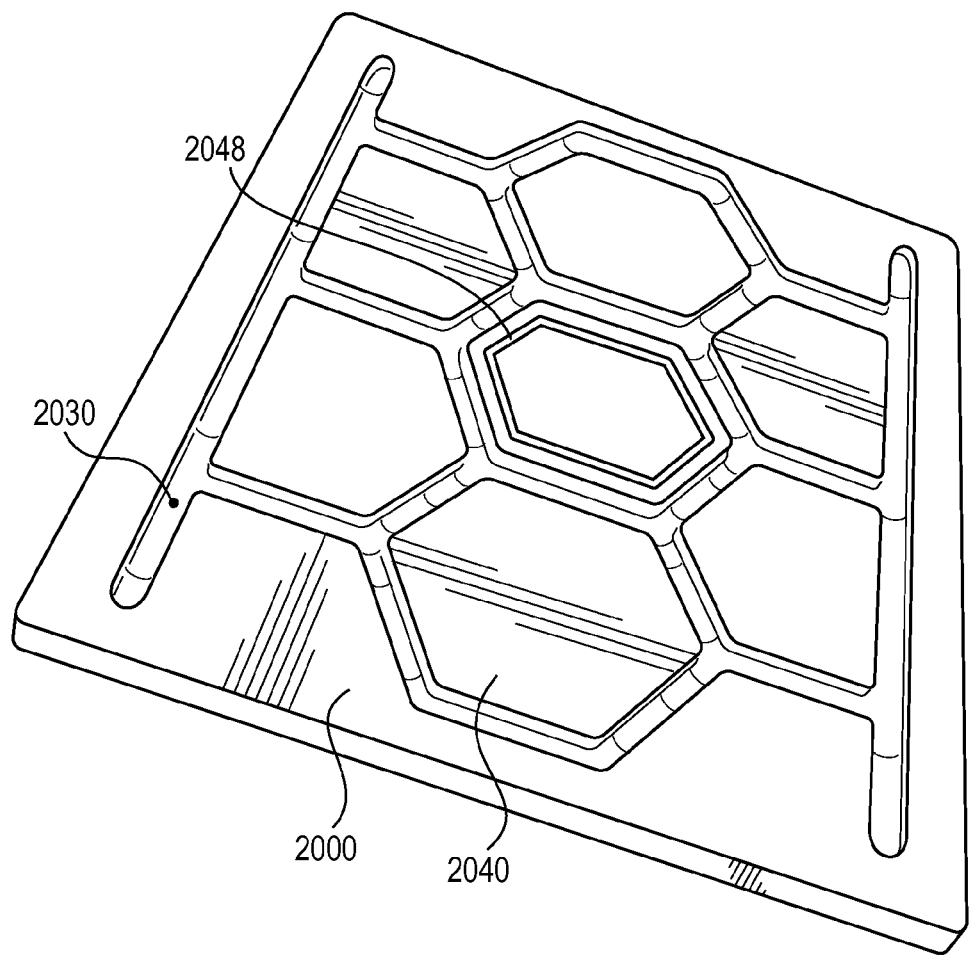
FIG. 7 is a perspective view of a fixture for manufacturing a scaffold for use in a device for selective rigidity.

FIG. 7 depicts a fixture 2000 for forming a scaffold 15. The fixture 2000 may be a flat board that includes a network of tunnels 2030 that are configured in the arrangement where the elongate pockets 30 (130, 230) are desired. The outermost surface of the fixture 2000 may include planar sections 2040 that are disposed where the windows 40 are desired. In some embodiments, the planar sections 2040 of the fixture 2000 may be heated to assist with the formation of the seams 48a, and/or to melt the opposite sheets 42, 44 forming the outer surface of the scaffold 15 together. In some embodiments, the fixture 2000 may include secondary tunnels 2048 that closely surround the tunnels 2030 to provide for placement of the wire or cord 48 to assist in defining the seams 48. As can easily be appreciated, to construct a scaffold, a first sheet 42 may be disposed upon the fixture 2000 and then the material (foam 52, pellets, foam 250, or a combination of these) is placed within the tunnels 2030 on top of the first sheet 42. A second sheet 44 is then placed on the fixture 2000 on the first sheet 42. The seams 48a may then be formed by an external tool, or in other embodiments, a second fixture 2000 contacts the second sheet 44 compressively and may form the seal 48a upon the application of heat. Upon formation of the scaffold 15, the scaffold 15 may then be fixed into the desired shape or orientation, and the vacuum line 28 attached to the pocket 30 to provide communication of suction from the vacuum line 28 to the pockets 30.

While the preferred embodiments of the disclosed have been described, it should be understood that the invention is not so limited and modifications may be made without departing from the disclosure. The scope of the disclosure is defined by the appended claims, and all devices that come within the meaning of the claims, either literally or by equivalence, are intended to be embraced therein.

The invention claimed is:

1. A device for obtaining selective rigidity with respect to a patient, comprising: a scaffold having a relaxed configuration and a rigid configuration, the scaffold comprising
    first and second opposing outer flexible layers that are sealed together to form a plurality of elongate pockets therein;
    a structure comprising an expandable foam or a plurality of particles disposed within the plurality of elongate pockets, and
    a vacuum port in fluid communication with the plurality of elongated pockets,
    wherein the structure further comprises a fluid-filled volume in the relaxed configuration and a reduced fluid-filled volume in the rigid configuration.

2. The device of claim 1, wherein the structure is configured to compress upon itself when in the presence of a suction force received at the vacuum port.

3. The device of claim 2, wherein the structure compresses upon itself due to a substantial collapsing of a plurality of voids associated with the structure.

4. The device of claim 1, wherein two or more pockets defining the plurality of elongate pockets are each in communication with each other and also in communication with the vacuum port such that a suction force communicates throughout the two or more pockets defining the plurality of pockets.

5. The device of claim 1, wherein the scaffold is disposed in a generally cylindrical configuration when fully expanded.

6. The device of claim 1, wherein the scaffold comprises a first closed end and a second open end, wherein the vacuum port is proximate to the second open end.

7. The device of claim 1, wherein the scaffold is disposed in a generally spherical configuration when fully expanded.

8. The device of claim 1, wherein the plurality of elongate pockets are oriented to define a plurality of windows formed from one or both of the first and second flexible layers disposed between the two or more of the plurality of elongate pockets.

9. The device of claim 8, wherein each of the plurality of windows are defined with the first and second layers sealed together.

10. The device of claim 8, wherein the plurality of windows are substantially transparent.

11. The device of claim 8, wherein one or more of the plurality of windows may be removed from the scaffold when the scaffold is in the relaxed configuration or the suction configuration.

12. The device of claim 1, wherein the plurality of elongate pockets are aligned with respect each other to form a honeycomb structure along outer walls of the scaffold.

13. The device of claim 1, wherein the elongate pockets comprise a foam structure disposed therein.

14. The device of claim 13, wherein the foam structure is configured to substantially collapse upon itself when in communication with a suction force.

15. The device of claim 13, wherein the foam structure is defined from elongate strips of foam disposed within the plurality of pockets.

16. The device of claim 13, wherein the foam structure is defined from a plurality of foam pellets distributed within the plurality of pockets.

17. The device of claim 1, wherein the scaffold defines a retractor.

18. The device of claim 17, wherein the retractor is configured for use within the peritoneal cavity.

19. The device of claim 17, wherein the scaffold is defined to be deployable into a working area of a patient through a laparoscopic port, wherein the vacuum port extends out of the laparoscopic port.

20. The device of claim 1, wherein the scaffold defines a stent.

* * * * *

UNITED STATES PATENT AND TRADEMARK OFFICE
CERTIFICATE OF CORRECTION

PATENT NO. : 9,445,801 B2  
APPLICATION NO. : 14/203007  
DATED : September 20, 2016  
INVENTOR(S) : Jeffrey S. Melsheimer Page 1 of 1

It is certified that error appears in the above-identified patent and that said Letters Patent is hereby corrected as shown below:

On the Title Page

Left Column, item (73), replace "Bllomington," with --Bloomington,--.

Signed and Sealed this  
Thirty-first Day of January, 2017

Michelle K. Lee  
*Director of the United States Patent and Trademark Office*